United States Patent [19]

McCaulay

[11] 4,288,649

[45] Sep. 8, 1981

[54] ISOBUTYLENE POLYMERIZATION PROCESS

[75] Inventor: David A. McCaulay, Homewood, Ill.

[73] Assignee: Standard Oil Company (Indiana), Chicago, Ill.

[21] Appl. No.: 154,943

[22] Filed: May 30, 1980

Related U.S. Application Data

[63] Continuation-in-part of Ser. No. 69,097, Aug. 23, 1979, abandoned, which is a continuation-in-part of Ser. No. 941,086, Sep. 11, 1978, abandoned.

[51] Int. Cl.$^3$ .............................................. C07C 2/02
[52] U.S. Cl. ................................................. 585/533
[58] Field of Search ............................. 585/532, 533

[56] References Cited

U.S. PATENT DOCUMENTS

| | | | |
|---|---|---|---|
| 3,268,618 | 8/1966 | Fletcher et al. | 585/533 |
| 3,296,331 | 1/1967 | Kovach | 585/533 |
| 3,464,929 | 9/1969 | Mitsche | 585/532 |
| 3,558,737 | 1/1971 | Saines | 585/533 |
| 3,607,959 | 9/1971 | Estes et al. | 585/533 |
| 3,717,586 | 2/1973 | Suqqitt et al. | 585/533 |

Primary Examiner—Curtis R. Davis
Attorney, Agent, or Firm—Mark DiPietro; William T. McClain; William H. Magidson

[57] ABSTRACT

A process for producing viscous polyisobutylene which comprises polymerizing isobutylene in a liquid phase using a halided alumina catalyst.

16 Claims, No Drawings

ISOBUTYLENE POLYMERIZATION PROCESS

This application is a continuation-in-part of Ser. No. 69,097 filed Aug. 23, 1979, which is a continuation-in-part of Ser. No. 941,086, filed Sept. 11, 1978, both of which are now abandoned.

This invention relates to a process for the polymerization of isobutylene (2-methyl-propene) with a halided alumina catalyst. More particularly this invention relates to a polymerization process in which the isobutylene contained in an olefin or a petrochemical stream is selectively polymerized with substantially no copolymerization of other olefins or hydrocarbons with a halided alumina catalyst.

There has been great interest for many years in the production of polyisobutylene, a normally highly viscous, water white liquid at room temperature having a viscosity of about 100 to about 50,000 Saybolt Universal Seconds at 100° C., and a molecular weight of about 600 to about 10,000 and higher. Polyisobutylene can be used to improve the properties of a variety of substances such as adhesives, sealants, lubricants, fuels, insulating oils, inks, paints, plastics, rubber, paper, etc. A large quantity of polyisobutylene is used to alkylate benzene, phenol, maleic anhydride, etc. to produce intermediates for the manufacture of lubricant and gasoline additives. In lubricant additives' manufacture polyisobutylene having a number average molecular weight of greater than about 1,250, preferably 1,500, and preferably between about 1,900–5,000, is ideal to produce additives that are very soluble in oil and that have accompanying high activity.

Polyisobutylene can be polymerized from pure isobutylene, but the separation of isobutylene from olefin-containing steams present in petrochemical plants is expensive and technically difficult. Commonly, the so-called "C$_4$" or "B-B" (Butanes-Butenes) olefin stream from petrochemical cracking units containing varying proportions of ethane, ethene, propane, propene, isobutane, n-butane, 1-butene cis- and trans-2-butene, isobutylene (2-methyl-propene) and other saturated and unsaturated hydrocarbons of various molecular weights at somewhat lower concentrations is an economical source of isobutylene. In steam or thermal cracking units the isobutylene-containing stream can differ somewhat from other types of catalytic cracking streams, containing larger proportions of olefinic products and therefore somewhat higher concentrations of isobutylene. The isobutylene-containing stream can contain from less than 5 weight percent to greater than 75 weight percent of isobutylene in the presence of various other components depending on the nature and source of feed and the conditions of operation of the petrochemical cracking unit which produces the stream. After the polymerization of and subsequent removal of isobutylene from the olefin stream, the remainder of the stream can be used to make alkylate gasoline blending stock by alkylating isobutane with the olefins which remain. Alkylation gasoline is a valuable high octane blending stock, and removal of other olefins and hydrocarbons by copolymerization would lower the octane value of the gasoline. Therefore, a process which converts essentially all the isobutylene in a stream to polyisobutylene in the presence of isobutane, olefins and other various hydrocarbons without copolymerizing significant amounts of the other hydrocarbons and olefins is highly desired.

Some low molecular weight (200–600) polymer is inherently produced with the high molecular weight polymer. This low molecular weight material has some value in applications such as additives manufacture but production of large amounts of low molecular weight product would result in discarding and burning as fuel large amounts of the product. Therefore a process which maximizes the production of high molecular weight polymer is highly desired.

Conventional processes for the production of viscous polyisobutylene from isobutylene streams which use particulate aluminum chloride catalysis suffer from certain drawbacks. The conventional aluminum chloride polymerization process requires refrigeration to produce high molecular weight (1,900–2,300) polymers. For example, at 5° C. a viscous polyisobutylene having a molecular weight of about 2,000 and a viscosity of about 15,000 SUS at 100° C. is produced. Byproducts of the polymerization reaction include aluminum chloride catalyst complexes and "Red Oil." The aluminum chloride catalyst complex is an isobutylene aluminum chloride complex. The "Red Oil" impurity is formed as a result of the reaction of the aluminum chloride with the isobutylene producing a polyunsaturated hydrocarbon-aluminum chloride product. About 2 weight percent of "Red Oil" is produced in the polyisobutylene product. Both the aluminum chloride-isobutylene-complex and the "Red Oil" byproducts must be removed from polyisobutylene by a complicated washing, settling, and clay drum filtration scheme. Undesirable inorganic and organic chloride-containing compounds are produced by the reaction of the feed and polymerization products with the particulate aluminum chloride catalyst. Conventional aluminum chloride catalysts have a relatively low activity, generally from about 150 to 175 grams of polymer is produced per gram of chloride in the catalyst. The aluminum chloride catalyst is difficult to prepare. Commonly aluminum chloride is prepared by passing chlorine gas through molten aluminum. The difficulties of handling chloride gas and molten aluminum during the reaction process pose obvious problems.

In current commercial isobutylene polymerization using aluminum chloride catalysis the major product has a number average molecular weight about 1,900–2,300. Commonly lighter commercial products are made by polymerizing isobutylene at higher temperature or removing light product fractions from the heavy polymer and blending the desired product from the light and heavy material. With current aluminum chloride technology higher molecular weight (2,300–5,000) polymer is difficult to produce economically.

U.S. Pat. No. 3,268,618, teaches polymerization of alpha-olefins of the general formula R—CH=CH$_2$ including ethene, propene, 1-butene, 4-methyl-1-pentene, butadiene, isoprene and styrene using a chlorided alumina. The production of a broad range of molecular weights including monomers, dimers and trimers having 12–18 carbons and products having 18 carbons and greater, i.e., trimers of 4-methyl-1-pentene, are particularly desired. The process conditions as disclosed in the examples are: (1) elevated pressures using nitrogen to pressurize, and (2) elevated temperatures, about 100°–130° C. The process converts only from 31 to 54% of the monomer to product. The product is a very broad range of molecular weight ranging from 84 (monomer) comprising about 37 (wt)% of the product, to above 1,670, 4.9 (wt)% of the product. This patent does not disclose a process for the polymerization of isobutylene to the high molecular weight viscous polymers. This is not surprising, since at the conditions used in the examples isobutylene would not polymerize to desired viscous polymer product.

U.S. Pat. No. 3,558,737 also teaches the polymerization of $C_3$ and $C_4$ olefins particularly the alpha olefins, propene, 1-butene, 2-butene producing dimers, trimers, and tetramers using a chlorided alumina prepared from a gamma alumina with a low surface area. Reference is made to U.S. Pat. No. 3,268,618, discussed above, to show that polymers with molecular weights above 800 are not successfully produced.

However, Saines fails to produce a commercially useful high molecular weight (1,900–2,300) liquid polymer. In Examples I–III of Saines, the molecular weight of the polymer product ranges from 659 to 1,037, and only about 33 weight percent or less of the olefin feed is converted to viscous polymer. In Example III an added ½ part by volume of ethylene per part by volume of propylene increased the molecular weight to 1,037 from 930. Saines fails to expressly teach the polymerization of isobutylene. While, Saines teaches that $C_3$–$C_4$ olefins can be polymerized at these conditions, Saines is limited to normal olefins such as propylene, 1-butene, and 2-butene. In the Examples, Saines polymerizes propylene and 1-butene. Accordingly, Saines apparently teaches away from the use of isobutylene with a chlorided alumina catalyst. Saines also fails to teach that isobutylene can be selectively polymerized in the presence of other olefin monomers.

Both references discussed above suffer from the drawbacks that (1) the selective polymerization of isobutylene in the presence of other $C_2$–$C_4$ olefins is not taught, (2) the processes fail to produce conversions of monomer to polymer greater than about 30 to 50%, (3) products of polymers with relatively narrow, high molecular weight ranges are not disclosed, (4) the recovery of high molecular weight polymer requires a series of washings to remove the product, and (5) apparently an ethylene component is required to produce a product with a molecular weight in excess of 1,000.

A primary object of the invention is to improve processes for the polymerization of isobutylene with essentially complete conversion of isobutylene to high number average molecular weight, greater than about 1,250, polymer. A further object of the invention is to provide a process to maximize production of polymers having a number average molecular weight greater than about 1,500, preferably in the range of about 1,900–5,000. Another object of the invention is to selectively polymerize isobutylene in the presence of other $C_2$–$C_4$ monomers while copolymerizing substantially no other monomer. Another object of the invention is to avoid the problems inherent in aluminum chloride isobutylene polymerization such as production of "Red Oil" and aluminum chloride catalyst complex, chloride containing contaminants and complicated washing, settling, and filtering processes.

I have found that the objects of this invention can be obtained by a process for polymerizing isobutylene which comprises contacting an olefin stream feed comprising isobutylene at sufficient pressure to maintain the normally gaseous stream in liquid phase at temperatures of about −25° to 52° C. with a halided alumina catalyst. More particularly olefin or petrochemical streams containing about 5 to 75 (wt)% of isobutylene in the presence of other olefins and paraffins such as ethane, ethene, propane, propene, butane, isobutane, 1-butene, cis- and trans-2-butene, etc. when contacted with the halided alumina catalyst made from any available active alumina produce high molecular weight polyisobutylene with substantially no copolymerization of other olefins and hydrocarbons. Conventional catalytic, thermal and steam cracking units are economical sources of the olefin, "$C_4$" or "B—B" stream. The conditions which are disclosed herein are critical to producing high 1,250–10,000, preferably 1,500–5,000, molecular weight viscous polyisobutylene which can be produced with very high conversions of monomer and with substantially no copolymerization of other $C_2$–$C_4$ monomers. The undiluted liquid phase operates to provide at least four benefits: (1) the liquid phase permits rapid removal of heat of polymerization from the polymerization to promote high molecular weight, (2) the liquid phase continuously washes the polymer from the active polymerization site obviating a separate washing step to isolate polymer, (3) higher isobutylene concentration at the active site than in gas phase or solution phase produces greater conversions and higher molecular weight, (4) any active alumina can be used, and (5) high selectivity of high molecular weight polymer.

Briefly, the isobutylene-containing olefin stream feed which can contain 100 wt.% isobutylene or more commonly 5 to 75 (wt)% isobutylene and a variety of hydrocarbons including ethane, ethene, propane, propene, n-butane, isobutane, 1-butene, cis-and trans-2-butene, and minor amounts of various other olefinic and paraffinic hydrocarbons is contacted with a chlorided alumina in liquid phase at a temperature of −25° to 52° C. However, above 52° C. the proportion of light polymer exceeds 37% of the product. While these light products having a molecular weight of about 200–600 have some market value and are also useful in additive manufacture, a major portion of the light products would be discarded or burned as fuel. At 52°–100° C. the chlorided alumina catalyst experiences rapid deactivation and increased production of light polymer. At 100° C. no product with molecular weight above about 300 is produced and the activity of the catalyst is nil in less than 1 hour.

The halided aluminas which are used to catalyze a wide variety of petroleum conversion processes such as isomerization, reforming, hydroforming, hydrofining, etc. can be used as the polymerization catalyst. One example of a chlorided alumina isomerization catalyst, found in U.S. Pat. No. 3,449,264 which is expressly incorporated by reference herein, is produced by heating an active alumina at temperatures in the range of 400°–1,500° F. in a dry ambient for a period of time in the range of ½ to 1000 hours, including a substantial and activating concentration of at least one gas selected from the group consisting of chlorine containing compounds, derivatives of methane, including carbon tetrachloride and chloroform. The alumina can be combined with other materials such as nickel, molybdenum, noble metals, silica, boria, etc.

We have found for high molecular weight polymer and large conversions of isobutylene a chlorided alumina prepared from an alumina with relatively large pore diameters ranging from about 50 to about 400 Angstroms, preferably 100 to 300 Angstroms, large pore volumes of about 0.3 to about 1 milliliter per gram, and large surface areas from about 125 to about 350 square meters per gram (BET scheme) is preferred.

Light alumina having large pore diameters and large surface area permit rapid heat removal.

The haliding agent can be a single or multi-component gas or vapor at elevated, atmospheric, or reduced pressures. Preferably, the haliding agent is a chloriding agent mixed with air or an inert carrier gas diluent. Examples of the chloriding agent are chlorine gas, hydrogen chloride, methyl chloride, methylene chloride, chloroform, carbon tetrachloride, thionyl chloride, phosgene, sulfur monochloride, sulfur dichloride, dichlorodifluoro methane, hexachloro ethane, hexachloro acetone, hexachloro-1,3-butadiene, hexachlorocyclopentadiene, trichloroacetylchloride, chloral etc. The preferable chloriding agent is carbon tetrachloride vapor which contains about 92 weight percent chloride and is easily handled. Air or argon is the preferred carrier gas diluent for reasons of ease of use, availability and economy. The handling agent is preferably used at a concentration in the inert carrier gas from about 0.5 to about 10 weight percent based on the total weight of the gas. The alumina can be contacted at temperatures from about 100° C. to about 600° C. for a period of time from about 1 to about 24 hours. The alumina will acquire from about 0.01 to about 14.0 weight percent halide at these conditions. A halided alumina with about 1.0-10 wt.% halides based on the alumina is preferred and an alumina with about 6.0 to 9.0 weight percent halide on the alumina is most preferred for ease of production and high catalytic activity. A catalyst having highest polymerization activity and containing maximum amounts of halogen while maintaining the alumina structure is produced at a temperature from about 300° to about 400° C. Below this temperature the concentrations of halogen which can be incorporated into the alumina is minimized. Above this temperature, the structure of the alumina deteriorates and the decomposition of the alumina produces aluminum chloride which sublimes from the catalyst. A 4 percent by weight carbon tetrachloride in argon or air, when contacted with the alumina for 6 hours at about 375° C. produces a chlorided alumina containing from about 7 to about 8 weight percent halide. Apparently the reaction between the haliding agent and the alumina does not produce significant amounts of aluminum halide. However, the oxygen atoms and hydroxyl groups in the alumina are displaced randomly by halide atoms. The haliding process when properly done maintains the basic structure of the alumina which after haliding contains randomly placed active polymerization sites halogen bonded.

The catalyst becomes inactive in time and can be regenerated. The inactive catalyst contains hydrocarbons bound to active sites, and low halide content. To regenerate, the catalyst is washed to remove hydrocarbons with a hydrocarbon solvent such as pentane, hexane, etc., and the solvent is removed from the catalyst with an inert gas at ambient temperature. The remaining traces of hydrocarbon are burned from the catalyst at elevated temperature with an air stream, and the catalyst is re-halided at conventional haliding conditions.

In somewhat greater detail, the polymerization is conducted in liquid phase by maintaining the commonly gaseous monomers under pressure. Preferably the pressure is maintained by the hydrocarbon or olefin stream pressure without the use of external pressurizing gases such as nitrogen or other inert gases. The following discussion applies to all the streams used in polyisobutylene polymerization. The difference between partial pressure of isobutylene and the various components of the streams is relatively small, and the pressure necessary to maintain isobutylene streams in liquid phase arising in petrochemical plants will vary little from the partial pressure of pure isobutylene. At 0° C. the partial pressure of an isobutylene stream is about 22 psi absolute, requiring a pressure of at least about 7 psi gauge to maintain the feed in liquid form. At 32° C. the partial pressure is about 62 psi absolute requiring at least about 47 psi gauge. At 60° C. the partial pressure is 122 psi absolute requiring at least about 107 psi gauge. Little experimentation will identify the minimum pressure for liquid phase polymerization of any individual stream. The conversions of isobutylene are highest when the mole fraction of isobutylene is highest. The minimum liquefying pressure is increased by the presence of pressurizing inert gases or normally liquid diluents, therefore, both a nitrogen gas pressurizing agent and hydrocarbon solvent diluents are undesirable.

The polymerization is conducted at temperatures from about −25° C. to 52° C. The molecular weight of the polymer increases linearly with respect to the reciprocal of the absolute temperature times $10^3$, in other words molecular weight increases with decreasing temperature. A temperature in the range is chosen which will product polyisobutylene of the desired molecular weight. At 3° C. a polymer having a number average molecular weight of about 6,000 is produced, at 38° C. a polymer having a number average molecular weight of about 1,700 is produced, and useable polyisobutylene can be made with a molecular weight in the range of 600–900 at 52° C. However above 52° C. the proportion of light products is greater than 33% of the product. While these products have some value, the production of low value, low molecular weight products should be minimized.

The polymerization can be carried out in either batch phase or in continuous phase with the catalyst contained in a fixed reaction zone. The concentration of the following isobutylene feeds is based on pure isobutylene, not as a mixed "B—B" feed. In batch phase, the polymerization of 0.1 to 100 parts of isobutylene per part of catalyst is carried out until substantially no increase in viscosity is noted. In continuous phase about 0.1 to about 60 parts by weight of isobutylene in the isobutylene stream can be contacted with 1 part of catalyst. Preferably, for highest conversions, from about 0.5 to 30 parts of isobutylene are contacted per part of catalyst. The rate of isobutylene feed can be controlled depending on isobutylene concentration and to reduce the rate of feed as catalyst activity slowly decreases during the aging of the catalyst. At high feed rates (60–120 grams of feed per gram of catalyst) initial conversion of isobutylene is essentially 100%, but high reaction rates cause catalyst heating, rapid catalyst deactivation and low viscosity polymer.

In the batch mode, the catalyst is simply filtered from the product. In the continuous mode, the insoluble catalyst is contained in at least one reaction zone to permit the isobutylene stream to flow into the reaction zone to continuously contact the alumina catalyst and to permit the polyisobutylene product to flow from the reaction zone catalyst free. The reaction zone can comprise a plurality of reaction vessels each containing catalyst. Alternatively, the catalyst can be continuously added to the monomer and continuously filtered from the product.

The catalyst-free polymer product is purified of light hydrocarbons by vacuum fractionation. Unreacted paraffins such as isobutane and other olefins are removed along with small amounts of low molecular weight "gasoline-like" light products with molecular weights of about 200 to 600 boiling up to about 350° C. from the desired polymer along with minor amounts of free isobutylene. The high molecular weight bottoms of vacuum fractionators is the desired product and is usable in the form as it is recovered.

EXAMPLE I

A conventional chlorided alumina catalyst containing 7.0% by weight chloride, made from an alumina with a pore diameter of 120 Å, and surface area of 252 m²/g (BET) was stirred at 60 psig and 5° C. in a batch autoclave with 800 grams or 1,350 milliliters of an isobutylene mixture blended to simulate a "B—B" stream which contained 50 weight percent butane, 20 weight percent isobutylene, and 30 weight percent 1-butene. The catalyst was prepared by passing an air stream through carbon tetrachloride at 0° C. and passing this stream over the alumina for 7 hours at 375° C. The composition was maintained during polymerization at 5° C. and was stirred for 2 hours. At the end of this period the product was filtered to remove catalyst and was subjected to fractional distillation at 1 millimeter pressure. The product was recovered in two fractions displayed in Table I, a low molecular weight "gasoline" (molecular weight 200-600) and the desired heavy polymer product.

EXAMPLE II

Example I was repeated except with 0.93 grams of a pulverized aluminum chloride slurried in 30 milliliters of pentane in place of the chlorided alumina. At the end of the reaction the product was washed with water, an aqueous sodium hydroxide and dried. The product was then subjected to fractional distillation at 1 millimeter pressure.

EXAMPLE III

A continuous laboratory scale apparatus for the continuous polymerization of an isobutylene stream under pressure was provided. A high pressure gas cylinder containing the "B—B" stream composition was connected with steel tubing to a container of compound to remove water and acidic impurity. The pressure and flow rate of the "B—B" stream was measured and maintained at set rate by a flow meter and pressure valve mounted on the tubing. The commercial "B—B" catalytic cracking unit stream then flowed through steel tubing into a polymerization reactor which consisted of 0.5 inch O.D., 0.42 inch I.D., 18 inch long steel tube equipped with a thermocouple well. The catalyst bed inside the tube was 12 inches long and contained up to 7 grams of chlorided alumina catalyst in the annular space between the thermocouple well and the tube wall. The reactor was immersed in an ethylene glycol cooling jacket. The olefin feed passed into the reactor where the temperature was monitored by the thermocouple which controlled the temperature of the reaction with the coolant. The reactor exit was connected with steel tubing to a pressure relief valve where the product was returned to ambient pressure. The product was collected in a flask, and unreacted olefins and paraffins flashed from the product to be collected in a condenser cooled with a dry ice-acetone mixture. Seven grams of catalyst prepared in the same manner as the catalyst in Example I from a Kaiser light alumina having an average pore diameter of 120 Angstroms, surface area of 252 square meters per gram (BET scheme) containing 7 weight percent chloride was placed in the polymerization reactor. A butane-isobutylene stream containing 50 percent n-butane, 20 percent isobutylene, and 30 percent 1-butene, was passed through the catalyst at a rate of 9.5 grams of feed per milliliter of the reactor per hour at 5° C. at 60 psig. The average temperature of the catalyst bed was maintained during the polymerization run at 8° C. The catalyst was maintained in the tube with helical porous plugs. Water white polymer was produced during a 7.5 hour polymerization reaction. The product was collected and fractionally distilled at 1 mm pressure. The product was divided into three fractions: "gasoline," "low molecular weight polymer," and "heavy polymer" as displayed in Table II.

EXAMPLE IV

Example III was repeated at 3° C., 25° C., 32° C., 50° C., and 100° C. The product recoveries and product distribution are found in Table III.

EXAMPLE V

Example III was repeated for a period of 143 hours at a polymerization temperature of 32° C. The properties and product recovery obtained during the catalyst aging are shown in Table IV.

TABLE I

| Batch Conversion of an Isobutylene Mixture | | |
|---|---|---|
| Example | II | I |
| Feed | | |
| Wt. % Butane | 50 | 50 |
| Wt. % Butene | 20 | 20 |
| Wt. % isobutylene | 30 | 30 |
| Catalyst | | |
| Wt. Alumina (gm) | | 14.0* |
| | (0.93 gm AlCl₃) | |
| Wt. Chloride (gm) | | 1.0 |
| Product Distribution, Wt. % | (Pentane-free basis) | |
| Gasoline, Low M.W. fraction | 4.8 | 2.4 |
| Heavy polymer | 95.2 | 97.6 |
| Heavy Polymer Properties | | |
| Viscosity at 210° F., SSU | — | 53370 |
| No. Av. Molecular Wt., ($\overline{M}n$) | 2540 | 3294 |
| Wt. Av. Molecular Wt., ($\overline{M}w$) | 4907 | 6278 |
| Chloride in Products, ppm | | |
| In total products | 234 | 45 |
| In gasoline, Low M.W. fraction | 2158 | 10 |
| In heavy polymer fraction | 100 | 46 |

*Kaiser light alumina. Average pore diameter = 120Å. Surface area = 252 m²/g (BET scheme), or 360 m²/g (sum of pore surface area.)

TABLE II

| Fixed Bed Conversion of an Isobutylene Mixture Example III | | | |
|---|---|---|---|
| Feed Composition: Butane 50%; Isobutylene 20%; n-Butene 30% | | | |
| WHSV = 9.5 g feed per hr. per ml. of reactor volume | | | |
| Total Time on stream = 7.5 hrs. | | | |
| Catalyst: 9.0 g alumina with 6.0 wt % chloride | | | |
| Polymerization temperature: 5 to 8° C. | | | |
| Product Distribution | Wt. g | Wt. % | ppm Cl in Fraction |
| Gasoline (C₆ to 205° C.) | 5.4 | 4.3 | 562 |

TABLE II-continued
Fixed Bed Conversion of an Isobutylene Mixture
Example III

| | | | |
|---|---|---|---|
| Low M.W. polymer (205 to 320° C.) | 0.2 | 0.2 | 64 |
| Heavy Polymer | 118.6 | 95.5 | 86 |
| Total | 124.2 | 100.0 | |
| Heavy Polymer Properties | | | |
| Viscosity at 210° F. | | | |
| Centistokes | | 12620 | |
| SSU | | 58860 | |
| Wt. Average Molec. Wt. ($\bar{M}w$) | | 6661 | |
| Ultraviolet | | | |
| Monoene, mmoles per g. | | 0.318 | |
| Diene, mmoles per g. | | 0.00011 | |
| Triene, mmoles per g. | | 0.0 | |
| Red oil, % | | 0.01 | |
| Infrared | | | |
| Trisubstituted Olefin, mmoles/ml | | 0.1528 | |
| Vinylidene Olefin, mmoles/ml | | 0.0626 | |

TABLE III
Polymerization of Isobutylene Mixture
Effect of Catalyst Temperature

| EXAMPLE IV | A | B | C | D | E |
|---|---|---|---|---|---|
| Catalyst Temperatures, °C. | 3 | 25 | 32 | 52 | 100 |
| Average Activity per Cycle (g polymer per g cat per hr) | 1.0 | 1.5 | 1.7 | 1.5 | 0 |
| Yield of Polymer per Cycle (g polymer per g catalyst) | 80 | 120 | 212 | 60 | 0 |
| Product Distribution, Wt. % | | | | | |
| 95 to 205° C. | 1.2 | 3.8 | 3.2 | 13.8 | 71.2 |
| 205–370° C. | 0.5 | 1.8 | 2.2 | 23.1 | 28.8 |
| Heavy polymer (product) | 98.3 | 94.4 | 94.6 | 63.1 | 0 |
| Heavy Polymer Properties | | | | | |
| Viscosity (SUS @ 99° C.) | 288930 | 32122 | 15161 | 913 | — |
| $\bar{M}n$ | 6067 | 2658 | 2229 | 896 | — |
| $\bar{M}w$ | 10705 | 5144 | 3634 | 1238 | 284 |

TABLE IV
EXAMPLE IV
Polymerization of Isobutylene Mixture at 32° C. (90° F.)
Wt. Catalyst: 7.3 g (7 wt % Cl)

| Comp. of C$_3$–C$_4$ Wt % | Time on Stream, Hr | | | | |
|---|---|---|---|---|---|
| Feed | 0 | 0.97 | 4.08 | 9.95 | 15.02 |
| Propane | 1.26 | 1.10 | 1.02 | 1.02 | 1.01 |
| Propylene | .95 | 0.67 | 0.66 | .67 | .67 |
| Isobutane | 41.30 | 52.66 | 50.15 | 49.30 | 48.79 |
| n-Butane | 7.22 | 9.72 | 9.72 | 9.50 | 9.41 |
| 1-Butene | 13.60 | 16.15 | 16.78 | 16.60 | 16.70 |
| Isobutylene | 20.70 | 0.34 | 1.78 | 3.33 | 4.03 |
| t-2-Butene | 9.52 | 12.45 | 12.56 | 12.20 | 12.30 |
| c-2-Butene | 5.50 | 6.96 | 7.30 | 7.13 | 7.13 |
| Isobutylene Conv % | — | 98.6 | 93.0 | 90.0 | 83.8 |
| Reaction Rate over Period | | | | | |
| (g polymer/g cat. hr) | | 2.23 | 2.10 | 1.96 | 1.89 |
| Product Distillation | | | Product No. 1 | | |
| Gasoline & Light Polymer | 55.2g | = | 5.4 wt % | | |
| Heavy Polymer | 961.7g | = | 94.6 wt % | | |
| Total | 1016.9g | = | 100.0 wt % | | |
| Heavy Polymer | | | | | |
| $\bar{M}n$, Number Average Moles, Wt | | | 2229 | | |
| $\bar{M}w$, Wt average Molec Wt | | | 3634 | | |
| Viscosity at 210° F. | | | | | |
| Saybolt Seconds (SUS) | | | 16065 | | |

TABLE IV-continued
EXAMPLE IV

| Centistokes, C/s | | 3444 | |
|---|---|---|---|

Polymerization of Butane-Butene at 32° C. (90° F.)
Wt. Catalyst: 7.3 g (7 wt % Cl)

| Comp. of C$_3$–C$_4$ Wt % | Time on Stream, Hr. | | | | | |
|---|---|---|---|---|---|---|
| | 30.45 | 47.75 | 72.35 | 78.85 | 98.40 | 143.3 |
| Propane | 0.95 | 0.96 | 1.13 | 1.10 | 1.12 | 12.6 |
| Propylene | 0.63 | 0.64 | 0.78 | 0.76 | 0.77 | 0.95 |
| Isobutane | 48.40 | 47.80 | 48.60 | 48.70 | 48.50 | 41.30 |
| n-Butane | 9.33 | 9.20 | 8.82 | 8.83 | 8.69 | 7.22 |
| 1-Butene | 16.40 | 16.30 | 16.00 | 15.90 | 15.80 | 13.60 |
| Isobutylene | 5.25 | 6.31 | 6.60 | 6.68 | 7.67 | 20.70 |
| t-2-Butene | 12.00 | 12.00 | 11.40 | 11.40 | 11.10 | 9.52 |
| c-2-Butene | 7.06 | 7.01 | 6.60 | 6.61 | 6.37 | 5.50 |
| Isobutylene Conv % | 78.60 | 74.00 | 72.80 | 72.40 | 68.00 | 0.0 |
| Reaction Rate over Period | | | | | | |
| (g polymer/g cat. hr) | 1.78 | 1.67 | 1.64 | 1.64 | 1.54 | 1.17 |
| Product Distillation | | | | Product No. 2 | | |
| Gasoline & Light Polymer | | | 17.5g | = | 3.4 wt % | |
| Heavy Polymer | | | 514.8g | = | 96.6 wt % | |
| Total Heavy Polymer | | | 532.3g | = | 100.0 wt % | |
| $\bar{M}n$, Number Average Moles, Wt | | | | | 2191 | |
| $\bar{M}w$, Wt Average Molec Wt | | | | | 3537 | |
| Viscosity at 210° F. | | | | | | |
| Saybolt Seconds (SUS) | | | | | 15161 | |
| Centistokes, C/s | | | | | | |

Unexpected benefits arise from the disclosed polymerization process. The polymerization reaction can be run at about 20° C. higher temperature than the aluminum chloride polymerization process while producing equivalent molecular weight polymer. At higher temperatures the polymerization rate increases. A polyisobutylene having a molecular weight about 2000–6000 is produced using aluminum chloride at about 3°–5° C. while the equivalent polyisobutylene is produced by chlorided alumina at about 25° C. This temperature differential is a great benefit, greatly reducing the need for refrigeration to produce high quality polymer. The activity of the chlorided catalyst appears to be greater than the aluminum chloride. About 3032 grams of polymer can be produced per gram of chloride in the catalyst. As shown in comparative Example I, aluminum chloride can produce 175 and less grams of polymer per gram of chloride. The conversion of monomer to polymer of the chlorided catalyst process is greater than the aluminum chloride. An examination of Table I shows 97.6% of the feed was polymerized to high molecular weight product by the chlorided alumina compound compared with a 95.2% conversion of the feed by aluminum chloride. The solid insoluble chlorided alumina catalyst does not produce the undesirable byproducts produced by aluminum chloride reactions with the monomer. Therefore the soluble catalyst complex and "Red Oil" are not produced. The solid catalyst particles can be maintained in an insoluble fixed bed solid-state form and separation of the product from the insoluble alumina is inherently simple. The polymer leaves the alumina catalyst-free. The product produced by the halided alumina catalyst contains much less halide prior to subsequent purification. An examination of Table II shows (1) a very high conversion of olefin (95.5 wt%), (2) a low concentration of chloride (86 ppm), (3) a very low production of Red Oil contamination, (i.e. 1 part of Red Oil per 10,000 parts of polymer vs. 2 parts of Red Oil per 100 parts of polymer for $AlCl_3$) and (4) a high selectivity for high molecular weight product.

Examination of Table III shows the various molecular weight products can be produced at different operating temperatures. Table III also shows the inoperability of isobutylene polymerization at temperatures above about 60° C. At 100° C. no polymer having a molecular weight above about 400 is formed, the fraction boiling between 95° C.-205° C. molecular weight about 200 was 71.2% of the total yield.

The examination of Table IV shows operation of the polymerization technique for 143 hours. At 143 hours the catalyst is entirely deactivated, but 68 percent of the catalyst activity remains at 98 hours. In the Table, Product 1 refers to the product collected during the first 15 hours of operation. Product 2 refers to the product collected between the 30th hour and the 98th hour of operation.

I claim:

1. A process for producing viscous polyisobutylene having a number average molecular weight greater than about 1,250 which comprises contacting a normally gaseous olefin stream feed comprising isobutylene with a halided alumina at a temperature of about −25° to 52° C. at sufficient pressure to maintain the feed in a liquid phase.

2. The process of claim 1 wherein the isobutylene is present in the olefin stream feed at a concentration of about 5 to 75 wt% of the olefin stream feed.

3. The process of claim 2 wherein the olefin stream is the product of a catalytic, thermal, or steam cracking process.

4. The process of claim 1 wherein the viscous polyisobutylene has a number average molecular weight greater than about 1,500.

5. The process of claim 1 wherein the viscous polyisobutylene has a number average molecular weight about 1,900-5,000.

6. The process of claim 1 wherein the halided alumina catalyst is a chlorided alumina catalyst.

7. The process of claim 6 wherein the chlorided alumina is prepared from an alumina having a pore diameter of about 50-400 angstroms, a pore volume of about 0.3-1.0 milliliter per gram, and a surface area of about 125-350 square meters per gram.

8. The process of claim 6 wherein the alumina has a pore diameter of about 100-300 angstroms.

9. The process of claim 1 wherein the halided alumina contains about 1-10 wt.% halide based on the alumina.

10. The process of claim 1 wherein the halided alumina is contained in at least one reaction zone, the olefin stream is continuously contacted with the halided alumina zone and the polyisobutylene product is continuously withdrawn.

11. A process for producing viscous polyisobutylene having a number average molecular weight about 1,900-5,000 which comprises continuously contacting an olefin stream comprising isobutylene at a temperature of −25° to 52° C. at sufficient pressure to maintain the feed in liquid phase with a chlorided alumina in at least one reaction zone to form a polyisobutylene product and continuously withdrawing the polyisobutylene product from the reaction zone.

12. The process of claim 11 wherein the reaction zone comprises a plurality of reaction vessels.

13. The process of claim 11 wherein the chlorided alumina is prepared from an alumina having a pore diameter about 50-400 angtroms, a pore volume of about 0.3-1.0 milliliter per gram, and a surface area of about 125-300 square meters per gram.

14. The process of claim 13 wherein the alumina has a pore diameter of about 100-300 angstroms.

15. The process of claim 11 wherein the chlorided alumina has 1-10 wt.% of chloride based on thhe alumina.

16. A process for producing viscous polyisobutylene having a number average molecular weight greater than about 1,250 which comprises contacting an olefin stream feed comprising isobutylene with a halided alumina, at a temperature of about −25° to 52° C. at sufficient pressure to maintain the feed in a liquid phase, wherein the halided alumina contains randomly substituted halogen atoms bonded directly to aluminum atoms, produced by contacting an alumina at a temperature of about 100° C. to 600° C. with a gaseous haliding agent.

* * * * *

UNITED STATES PATENT OFFICE
CERTIFICATE OF CORRECTION

Patent No. 4,288,649          Dated   September 8, 1981

Inventor(s)  David A. McCaulay

It is certified that error appears in the above-identified patent and that said Letters Patent are hereby corrected as shown below:

Column 2, line 40, "chloride" should read --chlorine--.

Column 3, line 9, "1-butene, 2-butene" should read --1-butene, and 2-butene--.

Column 5, line 18, "handling" should read --haliding--.

Column 10, line 51, after "Centistokes, C/s" insert the number --3250--.

Column 12, line 42, "thhe" should read --the--.

Signed and Sealed this

Twenty-eighth Day of December 1982

[SEAL]

Attest:

GERALD J. MOSSINGHOFF

Attesting Officer

Commissioner of Patents and Trademarks